United States Patent
Belfance et al.

(10) Patent No.: US 9,855,577 B1
(45) Date of Patent: Jan. 2, 2018

(54) NEEDLE SILICONIZATION WITH CONTROLLED POSITIVE PRESSURE GAS FLOW

(71) Applicants: John Belfance, Phenix City, AL (US); Jonathan Carleton Alt, South Amboy, NJ (US); Renato Gross, Auburn, AL (US); Zachary Dean Freeman, Auburn, AL (US); Benjamin Hunt, Auburn, AL (US); John Ferguson, Opelika, AL (US)

(72) Inventors: John Belfance, Phenix City, AL (US); Jonathan Carleton Alt, South Amboy, NJ (US); Renato Gross, Auburn, AL (US); Zachary Dean Freeman, Auburn, AL (US); Benjamin Hunt, Auburn, AL (US); John Ferguson, Opelika, AL (US)

(73) Assignee: SiO2 Medical Products, Inc., Auburn, AL (US)

( * ) Notice: Subject to any disclaimer, the term of this patent is extended or adjusted under 35 U.S.C. 154(b) by 394 days.

(21) Appl. No.: 14/604,634

(22) Filed: Jan. 23, 2015

Related U.S. Application Data

(60) Provisional application No. 61/930,809, filed on Jan. 23, 2014.

(51) Int. Cl.
*B05C 3/02* (2006.01)
*A61L 31/14* (2006.01)
(Continued)

(52) U.S. Cl.
CPC ............ *B05C 3/02* (2013.01); *A61L 31/08* (2013.01); *A61L 31/14* (2013.01); *A61L 2400/10* (2013.01); *A61L 2420/02* (2013.01); *A61M 5/32* (2013.01); *A61M 2207/00* (2013.01); *A61M 2207/10* (2013.01)

(58) Field of Classification Search
USPC .............. 118/400, 406; 427/2.28, 430.1
See application file for complete search history.

(56) References Cited

U.S. PATENT DOCUMENTS

| | | | | |
|---|---|---|---|---|
| 3,335,700 A | * | 8/1967 | Di Grado ............... | A61M 5/00 118/215 |
| 3,870,015 A | * | 3/1975 | Brown .................... | B05D 1/18 118/56 |

(Continued)

*Primary Examiner* — Cachet Sellman
(74) *Attorney, Agent, or Firm* — David B. Gornish; Eckert Seamans Cherin & Mellott, LLC

(57) ABSTRACT

A process and apparatus for applying a needle lubricant to a syringe. The interface forces between the needle lubricant and the syringe at the tip of the needle are balanced by optimizing the flow rate of a positively pressurized gas that is delivered to the syringe. Such optimization prevents the formation of bubbles in the needle lubricant that is applied to the syringe, thereby providing a confluent, uniform and smooth lubricant coating on the exterior wall of the needle and prevents lubricant from contaminating inner portions of the syringe. The smooth and uniform lubricant coating may minimize dilation and glide forces and pain associated with the insertion of the needle into a patient's tissue. Additionally, a gas pulse may blows off the droplet of needle lubricant from the tip of the needle to further minimize dilation forces and associated patient pain.

10 Claims, 4 Drawing Sheets

(51) Int. Cl.
*A61L 31/08* (2006.01)
*A61M 5/32* (2006.01)

(56) References Cited

U.S. PATENT DOCUMENTS

| | | | | |
|---|---|---|---|---|
| 4,135,561 A | * | 1/1979 | Senelonge | G01N 35/1065 |
| | | | | 141/234 |
| 5,911,711 A | * | 6/1999 | Pelkey | A61L 31/10 |
| | | | | 427/387 |
| 6,117,480 A | * | 9/2000 | Spallek | A61L 29/085 |
| | | | | 118/404 |
| 6,399,153 B1 | * | 6/2002 | Kephart | B05C 3/20 |
| | | | | 205/118 |
| 6,497,916 B1 | * | 12/2002 | Taylor | B05C 3/09 |
| | | | | 427/2.24 |
| 6,709,708 B2 | * | 3/2004 | Dinh | B05C 3/09 |
| | | | | 118/404 |
| 2012/0301613 A1 | * | 11/2012 | Doker | A61M 5/329 |
| | | | | 427/248.1 |

* cited by examiner

NEEDLE SILICONIZATION WITH CONTROLLED POSITIVE PRESSURE GAS FLOW

BACKGROUND OF THE INVENTION

Various types of lubricants may be applied to injection devices that penetrate a patient's tissue. Moreover, needles, such as, for example, needles that are used in the injection or removal of drugs, blood, fluid, or other materials into/from a patient, may be lubricated. Such lubrication may reduce forces associated with the penetration of the needle into/though/from the patient's tissue. For example, by lubricating needles with a needle lubricant, the force needed to open the initial point incision in a patient from the tip of the needle point over the beveled area of the needle point, also referred to as the dilation force, may be minimized. Further, the needle lubricant may also help minimize the force needed to insert the needle to a desired tissue depth in a patient once the needle is inserted past the bevel of the needle point, also referred to as the glide force. Such reductions in dilation and glide forces may allow for a reduction in patient pain that may be associated with the insertion into, and movement of the needle in, the patient's tissue.

Needle lubricants often used to lubricate needles, such as, for example (but not limited to), silicone lubricants that are heat curable, solvent curable, UV curable, or curable in other manners, typically include more than just silicone alone. Such lubricants also typically include carrier solvents and other components, including, for example, volatile organic compounds (VOC), silicone oil, components of the silicone oil, and solvent mix, among solvents and/or components. Yet, such carrier solvents and components may find their way to an interior region of the needle and/or an interior area of a barrel that is in fluid communication with the needle. Further, these contaminants may enter into these interior and inner regions and areas in various phases, such as, for example, as either a liquid, gas or vapor. Yet, when inside the needle or barrel, these solvents and components of the needle lubricant may be deemed undesirable contaminants. For example, such contaminants may negatively impact downstream manufacturing processes, such as the application of coatings to the barrel. The presence of the needle lubricant, or components thereof, may also be contaminants to the drug or other solution(s) that is to be injected into the patient through the barrel and/or needle.

Further, when coating the exterior of the needle with the needle lubricant, such as silicone oil, it is often attempted to provide a confluent, thin, and constant coating thickness of the needle lubricant. However, often attempts to apply such coatings to needles while also preventing needle lubricant from entering into the interior region of the needle results in the formation of bubbles of needle lubricant around the exterior wall of the needle. The movement, sticking, and bursting of such bubbles to/on the exterior wall of the needle results in a rough, non-uniform coating of needle lubricant on the exterior of the needle. Such a non-uniform coating causes higher friction than a uniform coating when the needle is inserted into a patient's tissue, thereby providing non-optimized dilation and glide forces and the risk for an associated increase in patient pain. Additionally, when applying needle lubricant to the needle, there is the potential that a droplet of needle lubricant will form at the tip of the needle. This droplet can also cause an increase in the dilation force, thereby leading to increased patient pain.

BRIEF SUMMARY OF THE INVENTION

Accordingly, in one aspect, the invention is directed to a process for applying a liquid needle lubricant to at least one needle. The process includes flowing positively pressurized gas through an interior region of the needle at a pre-determined flow rate. The pre-determined flow rate is based on a point at which bubbles begin to form in the liquid needle lubricant from the positively pressurized gas when the needle is submerged in the liquid needle lubricant. The process further includes submerging the needle in the needle lubricant while the positively pressurized gas is flowing through the interior region.

Figure 1:
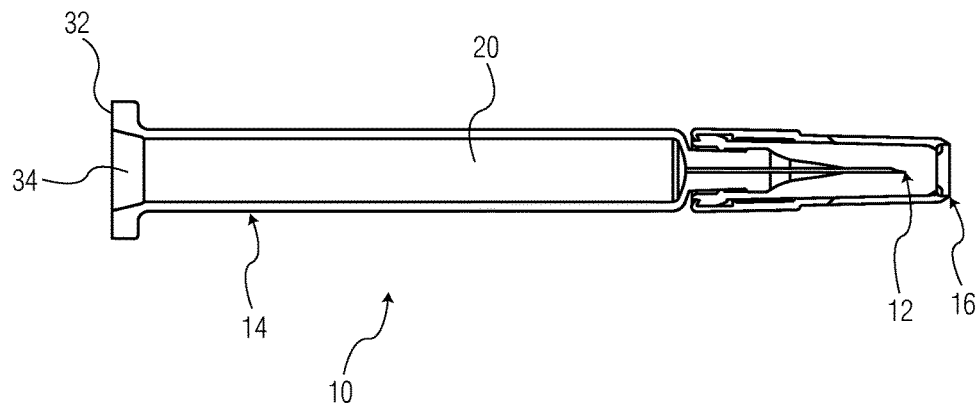
FIG. 1 illustrates a side cross sectional view of at least a portion of a syringe having a needle, barrel, and needle shield.

The foregoing summary, as well as the following detailed description of certain embodiments, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

The following reference characters are used in the specification and figures:

| | |
|---|---|
| 10 | Syringe |
| 12 | Needle |
| 14 | Barrel |
| 16 | Needle shield |
| 18 | Interior region (of needle 12) |
| 20 | Interior area (of barrel 14) |
| 22 | Wall |
| 24 | Tip |
| 26 | Bevel surface |
| 28 | Exterior surface |
| 30 | Interior surface |
| 32 | Proximal end |
| 34 | Opening |
| 50 | Lubrication stand |
| 51 | Supports |
| 52 | Reservoir |
| 53 | Base |
| 54 | Gas manifold assembly |
| 55 | Support plate |
| 56 | Manifold plate |
| 57 | Orifice (in support plate 55) |
| 58 | Manifold |
| 59 | Conduit |
| 60 | Gas inlet |
| 62 | Orifice |

| | |
|---|---|
| 64 | Retention plate |
| 66 | Seal |
| 68 | Clamp |
| 70 | Cover |
| 72 | Inner region (of manifold plate 58) |
| 74 | Seal |

DETAILED DESCRIPTION OF THE INVENTION

The present invention will now be described more fully with reference to the accompanying drawings, in which several embodiments are shown. This invention may, however, be embodied in many different forms and should not be construed as limited to the embodiments set forth here. Rather, these certain embodiments are examples of the invention, which has the full scope indicated by the language of the claims. Like numbers refer to like elements throughout.

Figure 2:
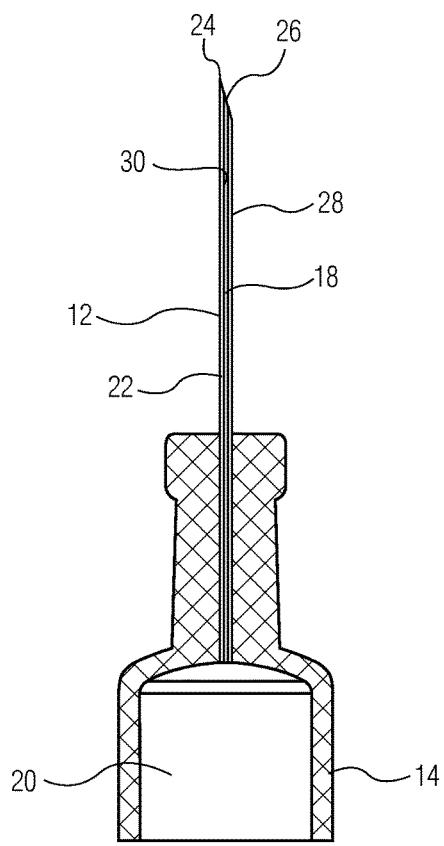
FIG. 2 is a cross sectional side view of a portion of a syringe in which a needle is exposed.

FIG. 1 illustrates a side cross sectional view of at least a portion of a syringe 10 having a needle 12 that is operably connected to a barrel 14. As shown in FIG. 2, according to the illustrated embodiment, the needle 12 is configured to be inserted into at least the tissue of a patient. An interior region 18 of the needle 12 is in fluid communication with an interior area 20 of the barrel 14 such that a fluid or drug in the barrel 20 may be dispensed from the syringe 10 and into the patient during an injection process. The barrel 14 includes an opening 34 positioned at a proximal end 32 of the barrel 14 and which is in fluid communication with the interior area 20 of the barrel 14.

FIG. 1 also illustrates the needle 12 being covered by a removable needle shield 16. Moreover, the needle shield 16 may be removed from the syringe 10 so as to expose the needle 12 so that the needle 12 may be inserted into a patient or other apparatus.

The needle 12 includes a wall 22 and a tip 24. The wall 22 generally defines the interior region 18 of the needle 12. Further, at least portion of the wall 22 is configured to provide a bevel surface 26 that extends to the tip 24. The wall 22 includes opposing exterior and interior surfaces 28, 30, the interior surface 30 being adjacent to the interior region 18. Further, the needle 12 may have a variety of shapes and sizes. For example, according to certain embodiments, the interior region 18 may have a diameter of approximately 0.18 millimeters (mm) and the wall 22 may have an outer diameter of approximately 0.40 millimeters (mm). However, other dimensions are contemplated.

The needle 12 may be coated with a needle lubricant in a variety of different manners, including, for example, one or a combination of the following: via a dip, wipe, spray, ultrasonic spraying, and/or cascade process, among other coating processes. For example, for a wipe process, a pad having a needle lubricant is wiped along the exterior surface 28 of the wall 22. With the spray process (normal or ultrasonic), the liquid needle lubricant is atomized so that small droplets of silicone oil are deposited on the exterior surface 28 of the wall 22. However, the particular process utilized may be configured to both prevent contaminants from entering into the needle 12 and/or barrel 14 while also being capable of applying an optimized coating of needle lubricant on the exterior surface 28 of the wall 22.

Figure 3:
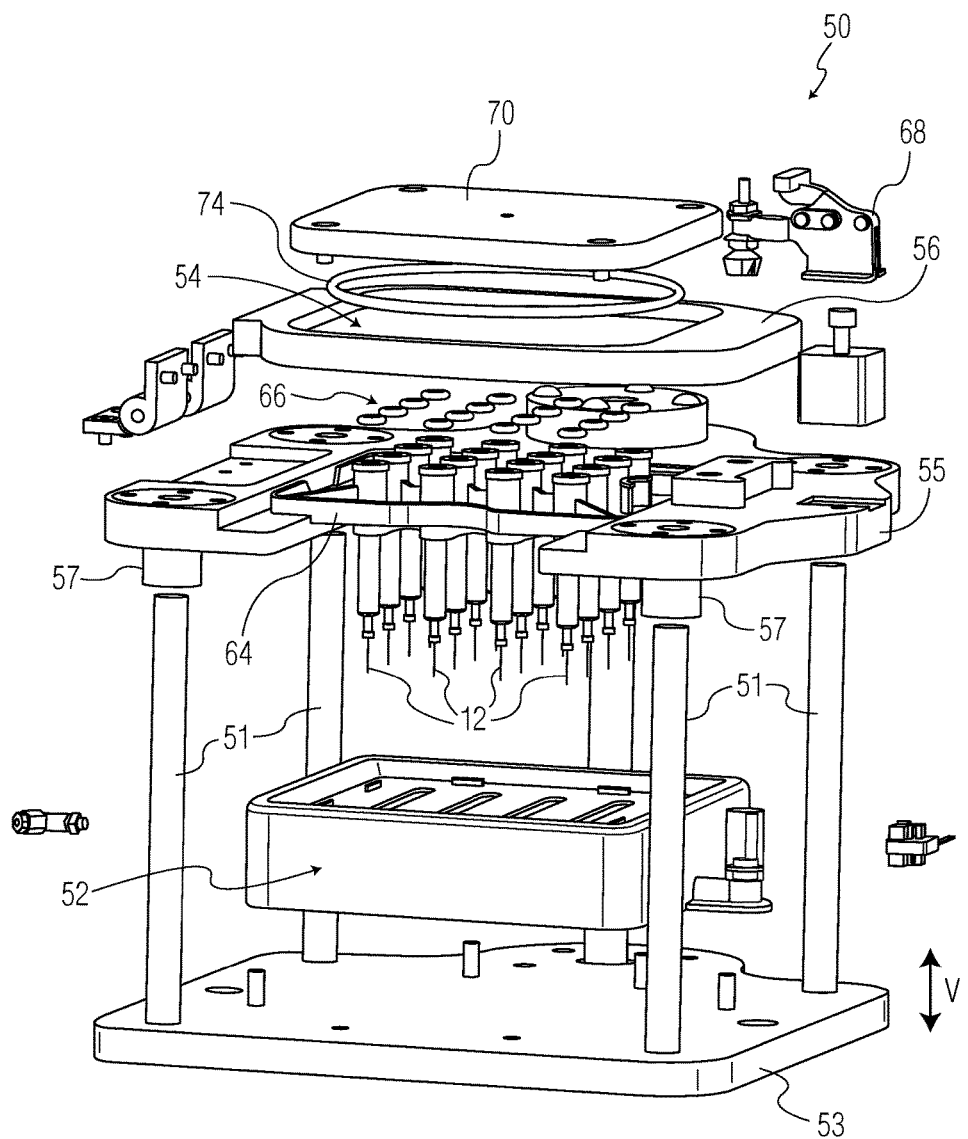
FIG. 3 is a front perspective view of a lubrication stand used to dip coat the needles of a plurality of syringes with a needle lubricant.

FIG. 3 illustrates a lubrication stand 50 used in dip coating needles 12 of one or more syringes 10 with a needle lubricant during a siliconization process. According to the illustrated embodiment, the lubrication stand 50 includes one or more supports or columns 51, a base 53, a reservoir 52, a support plate 55, a retention plate 64, and a gas manifold assembly 54. As shown, the supports 51 extend from the base 53.

The support plate 55 may be mounted to, or otherwise engaged with the supports 51. For example, the support plate 55 may include orifices 57 that are configured to receive the insertion of a corresponding support 51. Moreover, the orifices 57 may be configured to receive the slideable insertion of the support plate 55 so that the support plate 55 may be displaced along the supports 51. More specifically, according to the illustrated embodiment, the support plate 55 may be configured to be vertically displaced (as indicated by "V" in FIG. 3) along the supports 51 so as to adjust the position of the support plate 55 relative to the reservoir 52 to facilitate dip coating and removal of the needles 12 from the needle lubricant in the reservoir 52. Vertical movement of the support plate 55 may be accomplished, e.g., manually, pneumatically, with a spring-loaded actuator, a stepper motor, or other automation devices.

The support plate 55 may be configured for removable engagement with the retention plate 64. For example, referencing FIG. 3, the support plate 55 may include recessed surface that is configured to receive the placement of the retention plate 64. Further, according to the illustrated embodiment, the retention plate 64 is configured to receive, and hold, a plurality of syringes 10 in a position that allows the openings 34 of the syringes 10 to generally align with a corresponding orifice 62 in the manifold plate 56, as discussed below. For example, according to certain embodiments, the retention plate 64 may include a plurality of holes that are each configured to receive the slideable insertion of at least a portion of a syringe 10.

Figure 4A:
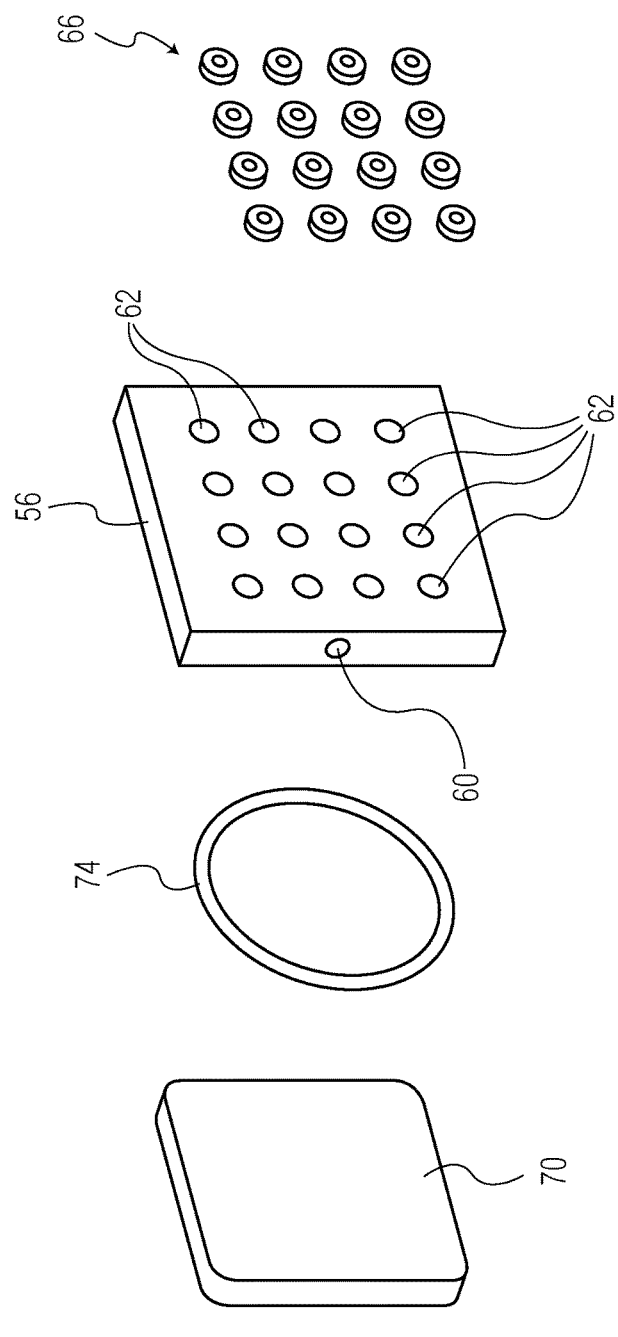
FIG. 4A illustrates an exploded view of a gas manifold assembly according to an illustrated embodiment of the present invention.

During the dip process, at least a portion of the needles 12 are submerged into needle lubricant that is contained in the reservoir 52. Further, the lubrication stand 50 includes a gas manifold assembly 54 that is used in the delivery of positively pressurized gas to the syringe 10, such as, for example, positively pressurized air. Referencing FIGS. 4A and 4B, according to certain embodiments, the gas manifold assembly 54 may include a manifold plate 56 that houses a manifold 58. The manifold 58 may include one or more pipes, tubes, and/or conduits 59 that are configured to assist in the delivery of the positively pressurized gas through the manifold assembly 54 and to the barrel 14. Additionally, according to certain embodiments, the manifold 58 may not be part of the manifold plate 56. More specifically, the manifold 58 and manifold plate 56 may or may not be part of a unitary construction.

Figure 4B:
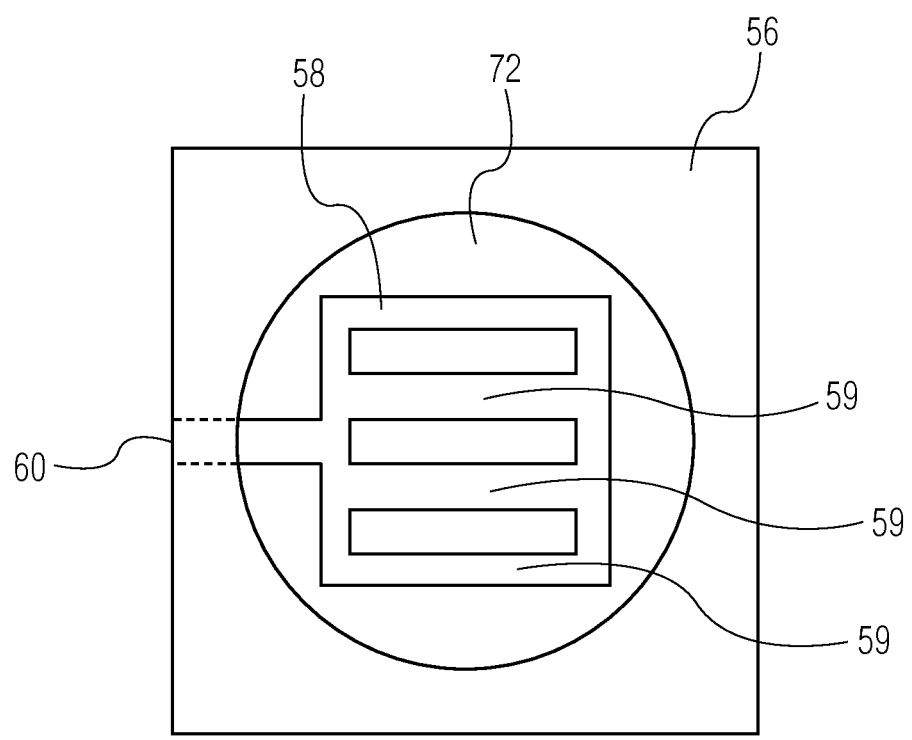
FIG. 4B illustrates a top view of an interior region of a manifold plate and a manifold according to an illustrated embodiment.

Further, as shown in FIGS. 3-4B, according to certain embodiments, the manifold assembly 54 may include a removable cover 70 that, when opened, may provide access in an inner region 72 of the manifold plate 56 and/or access to the manifold 58. When the cover 70 is in a closed position, such as when the cover 70 is operably secured to the manifold plate 56, a relatively air-tight seal between the cover 70 and the manifold plate 56, and/or a seal about the inner region 72, may be at least in part provided by a seal 74, such as, for example, a compressive seal.

The manifold 58 and/or manifold plate 56 may include a gas inlet 60 that receives the delivery of positively pressurized gas, e.g., house air (which is normally at 80-120 psi) reduced by a regulator preferably to under 1 psi. The positively pressurized gas may be delivered from the gas inlet 60 to the manifold 58 until being dispensed through orifices 62 in the manifold plate 56. The orifices 62 are configured to align with the openings 34 at the proximal ends 32 of the barrels 14 of the syringes 10 that are being held in the retention plate 64. Moreover, referencing FIG. 3, as previously discussed, the syringes 10 held in the retention plate 64 may be positioned to generally align with a corresponding orifice 62 in the manifold plate 56. A seal 66, such as an O-ring seal, for example, may be positioned between the proximal end 32 of the barrel 14 and the manifold plate 56 so as to prevent or minimize the release of the positively pressurized gas into the atmosphere as the positively pressurized gas travels through the orifice 62 and into the barrel 14. Further, the lubrication stand 50 and/or barrels 14 may be positioned such that the seals 66 are compressed between the proximal ends 32 of the barrels 14 of the syringes 10 and the manifold plate 56 so as to generally provide a relatively air-tight seal. For example, referencing FIG. 3, the lubrication stand 50 may include one or more clamps 68 that are configured to exert a force against the manifold plate 56 in the general direction of the syringes 10. More specifically, in the illustrated embodiment, the clamp 68 may provide a force that pushes or pulls the manifold plate 56 toward and/or against the syringes 10, thereby providing a force that at least assists in compressing the seals 66 that are positioned between the manifold plate 56 and syringes 10 to form a relatively air-tight seal.

The gas manifold assembly 54, including the seals 66, may be configured so that positively pressurized gas in the gas manifold assembly 54 is generally equally, and evenly, distributed at a low flow rate to the syringes 10 in the lubrication stand 50. Positively pressurized gas is provided to the syringes 10 prior to submersion of the needles 12 into needle lubricant contained in the reservoir 52. The appropriate level of gas pressure is determined based precisely on the point at which gas bubbles just begin to appear in the liquid needle lubricant from the gas that flows from the needles 12 immersed in the lubricant. As explained above, movement, sticking, and bursting of bubbles to/on the exterior wall of a needle results in a rough, non-uniform coating of needle lubricant on the needle's exterior wall. Thus, in one aspect, the present invention involves providing sufficient positive pressure to prevent the lubricant from migrating into interior portions of the needle (and possibly the syringe barrel) while at the same time not providing too much pressure that will result in formation of bubbles that compromise the uniformity of the lubricant's coating on the exterior wall of the needle. The inventors have found that providing a predetermined amount of positive pressure—particularly, just enough pressure until bubbles first begin to appear in the lubricant—strikes the appropriate balance. While the exact amount of positive pressure needed to meet this criterion may vary depending on a number of factors, it is generally contemplated that an optimal gas flow rate would be under 1 psi. Even distribution of the optimal amount of positively pressurized gas is key to enabling higher needle siliconization throughput. Without such even distribution, some needles may have lubricant migrate into their interior portions while other needles may have non-uniform siliconization due to bubbles that stick to and/or burst on the needles' exterior walls. Thus, even gas flow is necessary to have a scalable process.

According to the illustrated embodiment, the flow rate of the positively pressurized gas that is delivered from the gas manifold assembly 54 to the syringe 10 is generally optimized to minimize the formation of bubbles in the needle lubricant that has been applied to the needle 12. The optimal flow rate of the positively pressurized gas may be based on a variety of different factors, including, for example, one or more of: a needle property needle lubricant property, and/or coating condition. For example, needle properties may include, but are not limited to the physical size and configuration of the needle, such as for example the gauge of the needle, among other properties. Needle lubricant properties may include, but are not limited to, the components and viscosity of the lubricant. Coating conditions may include, but are not limited to, the temperature of the needle, needle lubricant, and/or the ambient air, and the humidity level of the ambient air. For example, according to certain embodiments in which the needle lubricant is a silicone oil that is mixed with a hexane based solvent (the VOC) and has a viscosity of about 1.0 to 10.0 centistokes (cts), the interior area 20 of the barrel 14 has an inner diameter of about 6.35 millimeters (mm), and the needle 12 is a 27 gauge needle, the optimal flow rate of the positively pressurized gas has been found to be about 0.25 to 0.8 pounds per square inch (psi), and more specifically 0.4 to 0.6 psi and nominally 0.5 psi. Moreover, at flow rates of the positively pressurized gas that are less than 0.25 psi, contamination in the form of needle lubricant being present in the interior region 18 of the needle 12 and/or the interior area 20 of the barrel 14 has been discovered. Further, bubbles within the needle lubricant have been discovered, via optical inspection, on the exterior surface 28 of the wall 22 of the needle 12 when flow rate of the positively pressurized gas is greater than 0.8 psi.

Additionally, according to certain embodiments, the lubrication stand 50 may be configured to provide a pulse of gas at the end of a siliconization cycle. More specifically, in the illustrated embodiment in which the needles 12 are coated using a dip coating process, after the needles 12 are removed from the reservoir 52 that contains the needle lubricant, a pulse of gas, also referred to as a gas pulse, may be delivered through the gas manifold assembly 54 and to the syringe 10 so as to blow off any droplet of needle lubricant that is present at the tip of the needle 12. For example, according to certain embodiments, a gas pulse of about 5.0 psi may be delivered through the gas manifold assembly 54 and to the syringe 10. Blowing off the droplet of needle lubricant from the tip of the needle 12 may at least assist in minimizing dilation forces and the associated pain experienced by the insertion of the needle 12 into a patient's tissue. Timing and other conditions relating to the gas pulse may be controlled with a microprocessor, as may be the entire dip coating process.

While the invention as described herein has been discussed primarily in the context of syringes, the invention may be implemented in any needle-based drug delivery device in which needle siliconization is desired, for example, auto-injectors and cartridges. Thus, processes and apparatuses that are described herein with reference to syringe barrels may be used with barrels of auto-injectors, cartridges or other needle-based drug delivery devices.

While the foregoing needle siliconization has been described with respect to a multi-up batch process, the process is also applicable for an inline flow. Additionally, as a flow through process, the needle siliconization described herein can also be executed in-line with a molding machine, with molded syringe barrels 14 being robotically removed from a molding machine and translated by track conveyor to the needle siliconization station in which the needle is coated while the positively pressurized gas flows through the needle 12 as a desired flow rate that prevents contamination of the syringe 10.

While the invention has been described in detail and with reference to specific examples thereof, it will be apparent to one skilled in the art that various changes and modifications can be made therein without departing from the spirit and scope thereof.

What is claimed is:

1. A process for applying a liquid needle lubricant to at least one needle comprising:
   flowing positively pressurized gas through an interior region of the needle at a pre-determined flow rate, the pre-determined flow rate being based on a point at which bubbles begin to form in the liquid needle lubricant from the positively pressurized gas when the needle is submerged in the liquid needle lubricant; and
   submerging the needle in the needle lubricant while the positively pressurized gas is flowing through the interior region.

2. The process of claim 1 wherein the pre-determined flow rate of the positively pressurized gas is less than 1 pound per square inch.

3. The process of claim 1, wherein the pre-determined flow rate of the positively pressurized gas is about 0.25 to 0.8 pounds per square inch.

4. The process of claim 1, wherein the pre-determined flow rate of the positively pressurized gas is about 0.4 to 0.6 pounds per square inch.

5. The process of claim 1, wherein the pre-determined flow rate of the positively pressurized gas is about 0.5 pounds per square inch.

6. A process for applying a liquid needle lubricant to a plurality of needles comprising:
   flowing positively pressurized gas through interior regions of the needles at a pre-determined flow rate, the pre-determined flow rate being based on a point at which bubbles begin to form in the liquid needle lubricant from the positively pressurized gas when the needles are submerged in the liquid needle lubricant; and
   submerging the needles in the needle lubricant while the positively pressurized gas is flowing through the interior regions of the needles.

7. The process of claim 6, wherein the positively pressurized gas is essentially evenly distributed between each of the plurality of needles.

8. The process of claim 6, wherein the pre-determined flow rate of the positively pressurized gas is less than 1 pound per square inch.

9. The process of claim 6, wherein the pre-determined flow rate of the positively pressurized gas is about 0.25 to 0.8 pounds per square inch.

10. The process of claim 6, wherein the pre-determined flow rate of the positively pressurized gas is about 0.5 pounds per square inch.

* * * * *